US00PP11138P

United States Patent [19]

Zary

[11] Patent Number: Plant 11,138

[45] Date of Patent: Nov. 30, 1999

[54] HYBRID TEA ROSE PLANT NAMED 'JACSEE'

[75] Inventor: Keith W. Zary, Thousand Oaks, Calif.

[73] Assignee: Bear Creek Gardens, Inc., Medford, Oreg.

[21] Appl. No.: 09/024,463

[22] Filed: Feb. 17, 1998

[51] Int. Cl.[6] ..... A01H 5/00

[52] U.S. Cl. ..... Plt./130

[58] Field of Search ..... Plt./130, 133, 102, Plt./141, 137

*Primary Examiner*—Howard J. Locker

*Attorney, Agent, or Firm*—Klarquist Sparkman Campbell Leigh & Whinston, LLP

[57] ABSTRACT

Hybrid tea rose plant having strong fragrance; large flowers presented singly; glossy, powdery mildew resistant foliage; vigorous, upright growth; and dense foliage.

1 Drawing Sheet

The present invention relates to a new and distinct variety of rose plant of the hybrid tea class which was originated by me by crossing an unnamed, rose-red hybrid tea seedling, the parentage of which is an unnamed red hybrid tea seedling× unnamed lavender hybrid tea seedling, with 'JACsos' (U.S. Plant Pat. No. 8,235).

The primary objective of this breeding was to produce a new rose variety having the strong scent, large hybrid tea flowers and upright growth of the unnamed female parent combined with the glossy, dense foliage and vigorous growth of the male parent, 'JACsos'. The objective was substantially achieved, along with other desirable improvements, as evidenced by the following unique combination of characteristics that are outstanding in the new variety and that distinguish it from its parents, as well as from all other varieties of which I am aware:

1. Strong fragrance;
2. Large flowers;
3. Glossy, powdery mildew resistant foliage;
4. Vigorous, upright growth;
5. Dense foliage;
6. Flowers presented one per stem.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticutural Society (London) Colour Chart, except where ordinary dictionary significance of color is indicated.

Parentage:

*Seed parent.*—Unnamed, rose-red hybrid tea seedling, the parentage of which is unnamed red hybrid tea seedling×unnamed lavender hybrid tea seedling.

*Pollen parent.*—'JACsos' (U.S. Plant Pat. No. 8,235).

Classification:

*Botanical.*—Rosa hybrida.

*Commercial.*—Hybrid tea.

FLOWER

Observations made from specimens grown in a garden environment at Somis, Calif. from March, 1996 to December, 1997.

Blooming habit: Recurrent.

Bud:

*Size.*—1½" long when the petals start to unfurl.

*Form.*—The bud form is long, pointed ovoid.

*Color.*—When sepals first divide, bud color is White Group 155D with occasional blotches of Red Group 55B. When half blown, the upper sides of the petals are White Group 155D with petals edged in Red Group 55B and a light blush over the white of Red Group 56B and the lower sides of the petals are White Group 155D.

*Sepals: Color: Green Group* 138B. Surface texture: Covered in fine hairs. There are three normally to heavily appendaged sepals. There are two unappendaged sepals with hairy edges.

*Receptacle.*—Color: Green Group 139B. Shape: Funnel. Size: Medium (5/16"×¼"). Surface: Smooth.

*Peduncle.*—Length: Medium (3"). Surface: Smooth. Color: Medium green. Strength: Stiff, erect.

Bloom:

*Size.*—Large. Average open size is 4".

*Borne.*—Singly.

*Stems.*—Medium (16–18"), strong.

*Form.*—When first open: High centered. Permanence: Flattens, outer petals curl back.

*Petalage.*—Number of petals under normal conditions: 25—30.

*Color.*—The upper sides of the petals are White Group 155D edged in Red Group 55B with a light blush over the white of Red Group 56B. The reverse sides of the petals are White Group 155D. The base of each petal has a Yellow Group 3C half moon (3/16×3/16") at the point of attachment. The major color on the upper sides is White Group 155D.

*Variegations.*—There are occasional greenish streaks on the guard petals.

*Discoloration.*—At the end of the first day: No change. At the end of the third day: No change. By day six or seven fades to pure white.

*Fragrance.*—Strong.

Petals:

*Texture.*—Thick.

*Shape.*—Round to deltoid.

*Form.*—Tips slightly recurved.

*Arrangement.*—Imbricated. Petaloids in the center are few.

*Persistence.*—Petals drops off cleanly before drying.

*Lastingness.*—On the plant: Long (7– 8 days). As a cut flower: Long (9–10days).

Reproductive Parts:

*Anthers.*—Size. Medium. Quantity: Many. Color: Yellow. Arrangement. Regular around styles.

*Filaments.*—Color: Yellow.

*Pollen.*—Color: Gold yellow.

*Styles.*—Color: Reddish.

*Stigmas.*—Color: Greenish white.

Plant:

*Form.*—Bush.

*Growth.*—Vigorous; upright; branching: Height of mature plant is five feet, width is four feet.

Foliage: Number of leaflets on normal mid-stem leaves: Five.

*Size.*—Large (5½ to 6"×4 to 4½").

*Quantity.*—Abundant.

*Color.*—New foliage: Upper and lower sides Greyed Red Group 178A. Old foliage: Upper side: Green Group 139A. Lower side: Green Group 139C.

Leaflets:

*Shape.*—Pointed oval.

*Texture.*—Upper side: Leathery, glossy.

*Edge.*—Serrated.

*Serration.*—Single, small.

*Petiole Rachis.*—Color: Reddish (upper surface); green on lower surface.

*Petiole Underside.*—Smooth with occasional prickles.

*Stipules:*—Medium (½"), serrated, bearded.

*Diseases Resistance.*—Resistance to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Medium, hooked upward.

*Color when young.*—Red.

Small Prickles: On laterals: Many.

*Quantity.*—On main stalks: Many.

*Color.*—Reddish when young, then brown.

I claim:

1. A new and distinct variety of rose plant of the hybrid tea class substantially as herein shown and described, characterized particularly by its strong fragrance; large flowers presented singly; glossy, powdery mildew resistant foliage; vigorous, upright growth; and dense foliage.

* * * * *

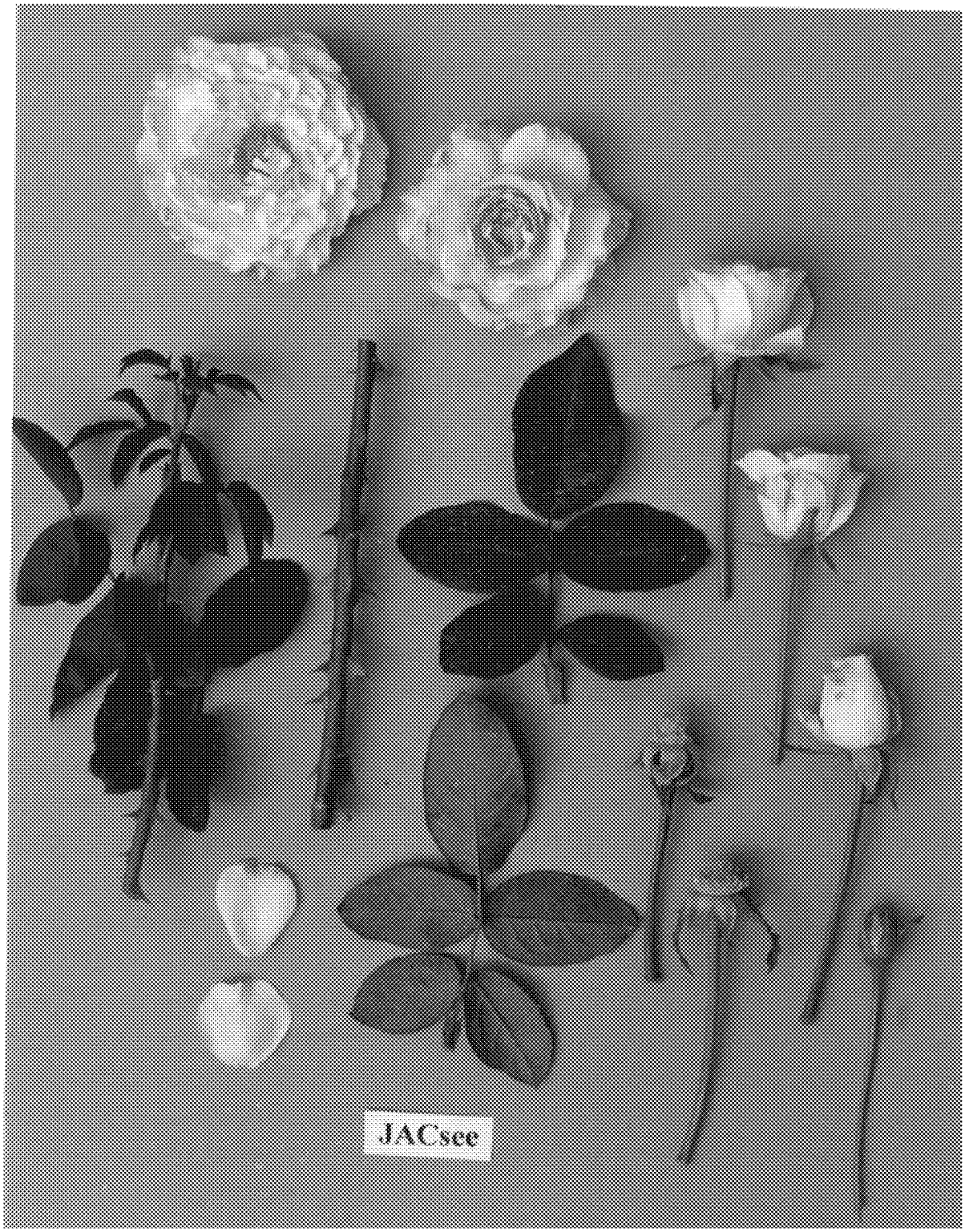
JACsee